(12) United States Patent
Essler et al.

(10) Patent No.: US 9,668,973 B2
(45) Date of Patent: Jun. 6, 2017

(54) COMPONENTS FOR PRODUCING AMPHOTERIC LIPOSOMES

(71) Applicant: Marina Biotech, Inc., Bothell, WA (US)

(72) Inventors: Frank Essler, Halle (DE); Steffen Panzner, Halle (DE); Gerold Endert, Halle (DE)

(73) Assignee: Marina Biotech, Inc., Bothell, WA (US)

(*) Notice: Subject to any disclaimer, the term of this patent is extended or adjusted under 35 U.S.C. 154(b) by 396 days.

(21) Appl. No.: 14/052,215

(22) Filed: Oct. 11, 2013

(65) Prior Publication Data

US 2014/0227345 A1    Aug. 14, 2014

Related U.S. Application Data

(63) Continuation of application No. 13/291,650, filed on Nov. 8, 2011, now Pat. No. 8,580,297, which is a continuation of application No. 10/505,093, filed as application No. PCT/EP03/01662 on Feb. 19, 2003, now abandoned.

(30) Foreign Application Priority Data

Feb. 19, 2002  (DE) .................................. 102 07 178

(51) Int. Cl.
| | |
|---|---|
| *A61K 9/127* | (2006.01) |
| *A61K 47/24* | (2006.01) |
| *A61K 31/495* | (2006.01) |
| *C07D 295/00* | (2006.01) |
| *C07C 229/16* | (2006.01) |
| *C07C 229/24* | (2006.01) |
| *C07D 233/64* | (2006.01) |
| *C07F 9/6506* | (2006.01) |
| *C07K 5/06* | (2006.01) |
| *C07K 5/08* | (2006.01) |
| *C12N 15/88* | (2006.01) |
| *A61K 47/18* | (2017.01) |
| *A61K 47/22* | (2006.01) |
| *A61K 31/5375* | (2006.01) |

(52) U.S. Cl.
CPC ............ *A61K 9/127* (2013.01); *A61K 9/1271* (2013.01); *A61K 9/1272* (2013.01); *A61K 47/183* (2013.01); *A61K 47/22* (2013.01); *A61K 47/24* (2013.01); *C07C 229/16* (2013.01); *C07C 229/24* (2013.01); *C07D 233/64* (2013.01); *C07F 9/65067* (2013.01); *C07K 5/06191* (2013.01); *C07K 5/0827* (2013.01); *C12N 15/88* (2013.01); *A61K 31/495* (2013.01); *A61K 31/5375* (2013.01); *C07D 295/00* (2013.01); *Y10T 428/2991* (2015.01)

(58) Field of Classification Search
None
See application file for complete search history.

(56) References Cited

U.S. PATENT DOCUMENTS

| | | | |
|---|---|---|---|
| 4,788,182 A | 11/1988 | Baschang et al. | |
| 6,022,720 A | 2/2000 | Martinou et al. | |
| 6,043,094 A * | 3/2000 | Martin ................. | A61K 9/1273 424/450 |
| 6,090,800 A | 7/2000 | Unger et al. | |
| 6,180,134 B1 * | 1/2001 | Zalipsky .............. | A61K 9/0019 424/450 |
| 6,379,698 B1 | 4/2002 | Leamon | |
| 8,580,297 B2 * | 11/2013 | Essler ................. | A61K 9/1271 424/450 |
| 2001/0033862 A1 | 10/2001 | Hostetler et al. | |

FOREIGN PATENT DOCUMENTS

| | | |
|---|---|---|
| EP | 0588289 A2 | 3/1994 |
| WO | WO-0059474 A1 | 10/2000 |

OTHER PUBLICATIONS

Signaling-Gateway Interleukin 6 (http://www.signaling-gateway.org/molecule/query7afcsicUA004204) 1 page. Downloaded from Internet on Mar. 7, 2011.*
JD Radolf, LL Arndt, DR Akins, LC Curetty, ME Levi, Y Shen, LS Davis, MV Norgard. "Treponema pallidum and Borrelia burgdorferi and Synthetic Lipopeptides Activate Monocytes/Macrophages/Lipoproteins." The Journal of Immunology, vol. 154, 1995, pp. 2866-2877.*
CAS Registry Record for 305-84-0. Entered STN Nov. 16, 1984. 1 page.
Heyes, J.A. et al., "Synthesis of Novel Cationic Lipids: Effect of Structural Modification on the Efficiency of Gene Transfer", *Journal of Medicinal Chemistry*, 45:99-144 (2002).
Holliday, R. et al., "A Role for Carnosine in Cellular Maintenance," *Biochemistry*, 65:843-848 (2000).
Signaling-Gateway Interleukin 6 (http://www.signaling-gateway.org/molecule/query?afcsid=A004204) 1 page. Mar. 7, 2011.
Zalipsky, S. et al., "Poly(ethylene-glycol)-Grafted Liposomes with Oligopeptide or Oligosaccharide Ligands Appended to the Termini of the Polymer Chains," *Bioconjugate Chemistry*, 8:111-118 (1997).

* cited by examiner

*Primary Examiner* — Isaac Shomer
(74) *Attorney, Agent, or Firm* — Eckman Law Group

(57) ABSTRACT

The invention suggests amphoteric lipids wherein one or more amphoteric groups having an isoelectric point between 4 and 9 are substituted on a membranous or membrane-forming amphiphilic substance, as well as liposomes containing such compounds.

5 Claims, 1 Drawing Sheet

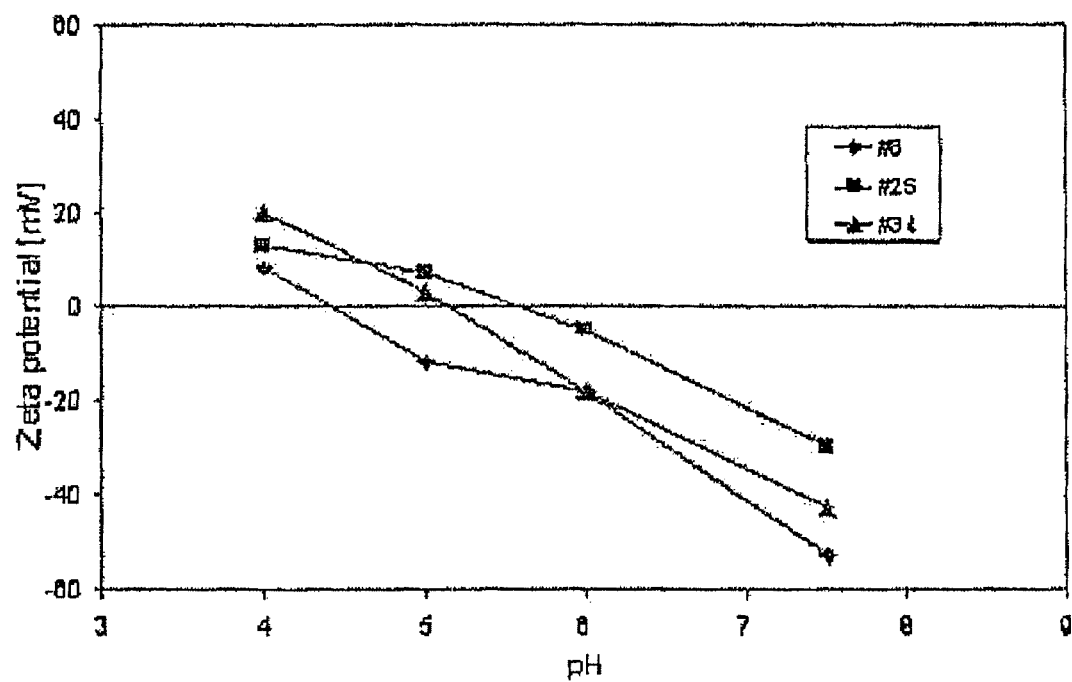

COMPONENTS FOR PRODUCING AMPHOTERIC LIPOSOMES

The invention relates to amphoteric compounds based on amphiphilic molecules, the head groups of which being substituted with one or more amphoteric groups having an isoelectric point between 4 and 9, to liposomes containing such compounds, and to the use thereat.

The term "lipids" summarizes three classes of natural materials which can be isolated from biological membranes: phospholipids, sphingolipids, and cholesterol, including its derivatives. Industrially produced compounds with similar properties are diacylglycerols or N,N-dialkylamines.

These substances are of technical interest in the production of liposomes. Inter alia, such liposomes can be used as containers for active substances in pharmaceutical preparations. In such uses, efficient and stable packaging of the cargo and controllable release of the contents are desirable. Both of these requirements are not easy to combine: the more stable and compact the packaging, the more difficult the release of the entrapped active substance therefrom. For this reason, liposomes changing their properties in response to an external stimulus have been developed. Thermosensitive and pH-sensitive liposomes are well-known. The pH-sensitive liposomes are of special interest, because this parameter undergoes changes even under physiological conditions, e.g. during endocytotic reception of a liposome in a cell, or during passage of the gastrointestinal tract.

According to the prior art, pH-sensitive liposomes particularly comprise cholesterol hemisuccinate (CHEMS). Cholesterol hemisuccinate, in mixture with phosphatidyl ethanolamine, is used to produce pH-sensitive liposomes (Tachibana et al. (1998); BBRC 251, 538-544, U.S. Pat. No. 4,891,208). Such liposomes can enter cells by endocytosis and are capable of transporting cargo molecules into the interior of cells on this route, without doing damage to the integrity of the cellular membrane.

One substantial drawback of CHEMS is its anionic character. Liposomes produced using same have a negative overall charge, being taken up by cells with low efficiency. Despite the transfer mechanism described above, they are barely suitable for the transport of macromolecules into cells. Furthermore, packaging of macromolecular active substances such as DNA in such liposomes is not possible.

For the transport of active substances into cells (transfection), the art uses cationic liposomes having a preferably high and constant surface charge. The positive overall charge of such particles leads to electrostatic adherence to cells and subsequently to efficient transport into same. The use of these compounds and of liposomes produced using same remains restricted to in vitro or ex vivo applications, because such positively charged liposomes result in uncontrolled formation of aggregates with serum components.

In WO 00/59474, the prior art describes compounds having a membrane anchor and a cationic and an anionic head group on the same molecule, the anionic group being linked to the basic structure via a disulfide bridge. The disulfide bridge can be reduced under physiological conditions, e.g. by contact with the cytosol, the anionic head group then is liberated, and the overall molecule assumes a positive charge, thereby enabling fusion with the cell membrane. The toxicity profile and storage stability of the compounds disclosed in WO 00/59474 are disadvantageous, because cleavage of the disulfide bridges results in free cationic lipids. Disadvantageously, these compounds are known to have a cytotoxic effect.

Furthermore, well-known lipids and liposomes comprising same are disadvantageous in that the amounts of proteins, DNA and/or RNA which can be bound or entrapped by same are below average. When modifying the liposomes so as to make them bind or entrap higher amounts of cargo, they will become cytotoxic or have low compatibility with serum or blood, or will be unstable in blood or serum because they would be attacked by particular components of the blood or serum, such as complement or perforin. Well-known liposomes and lipids therefore have only limited suitability for use in living organisms and, in addition, exhibit low efficiency in conveying ingredients and/or binding substances. Some of the well-known compounds lacking at least part of the above-mentioned drawbacks are very complicated to produce, some of the components being costly to such an extent that utilization on a clinical scale or use in laboratory routines is not possible.

BRIEF DESCRIPTION OF THE DRAWING

FIG. 1 shows the profile of the zeta potential in mV at varying pH values for amphoteric liposomes of this disclosure.

DETAILED DESCRIPTION OF THE INVENTION

The object was therefore to produce new compounds which would not exhibit the above-mentioned drawbacks and i) which, in particular, allow entrapping of active substances, particularly plasmids, in liposomes;

ii) from which liposomes can be produced which are capable of conveying an entrapped active substance into the interior of cells;

iii) the presence production of which aids to achieve the liposomes which can be mixed with serum under physiological conditions, with no aggregation taking place;

iv) which can be incorporated in high amounts in liposomal membranes;

v) which can be produced easily and at low cost.

The invention solves the above technical problem by means of liposomes comprising amphiphilic compounds according to general formula (I), which compounds have an isoelectric point between 4.5 and 8.5 and are capable of reversibly changing their state of charge from cationic to anionic within a pH range of 1-2 units:

Amphoteric substance-Y-spacer-amphiphilic substance     (I)

wherein
(a) the amphoteric substance has at least one portion of cationic charge with a pKa value between 4 and 8 and/or at least one portion of anionic charge with a pKa value between 3 and 7 and optionally additional charge carriers,
aa) said portion of cationic charge being selected from the group comprising imidazole, morpholine, piperazine, purine, pyridine and/or pyrimidine or derivatives thereof,
bb) said portion of anionic charge being a carboxyl group which comprises acetic acid, bromoacetic acid, chloroacetic acid, acetoacetic acid, propionic acid, acrylic acid, butyric acid, crotonic acid, or carboxylic acids bound in the aliphatic chain; which comprises dicarboxylic acids such as oxalic acid, malonic acid, maleic acid, fumaric acid, malic succinic acid, acid, tartaric acid, glutaric acid, adipic acid, caprylic acid, pimelic acid, suberic acid, cyclohexanedicarboxylic acid or cyclopentanedicarboxylic acid, mono-esterified or amidated or bound in the aliphatic chain; which comprises oligocarboxylic acids such as citric acid, isocitric acid or ethylenediaminetetraacetic acid, mono-esterified or amidated or bound in the aliphatic chain, (b) the spacer is a lower alkyl residue with up to 8 C atoms, with linear, branched or cyclic structure, with 0, 1 or 2 ethylenically unsaturated bonds, and 0-4 hydroxyl groups, (c) Y comprises —(C=O)—O—; —(C=O)—NH—; —NH—(C=O)—O—; —O—; —NH—; —CH=N—; —O—(O=C)—; —(O=C)—; —NH—(O=C)—; —O—(O=C)—NH—, —N=CH— and/or —S—S—, (d) the amphiphilic substance is a structure according to general formula (II) or (III) or (IV):

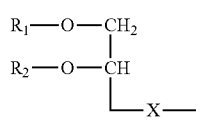

(II)

wherein
$R_1$ and $R_2$ independently are $C_5$-$C_{30}$ alkyl or acyl chains with 0, 1 or 2 ethylenically unsaturated bonds, and
X is selected from the group comprising —O—(C=O); —NH—(C=O)—; —S—(C=O)—; —O—; —NH—; —S—; —(O=C)—O—; —S—(O=C)—; —N=CH— and/or —S—S—;
or

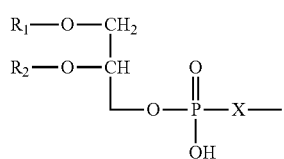

(III)

wherein
$R_1$ and $R_2$ independently are $C_8$-$C_{30}$ acyl chains with 0, 1 or 2 ethylenically unsaturated bonds, and
X is —O—;
or

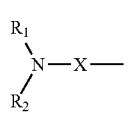

(IV)

wherein
$R_1$ and $R_2$ independently are $C_8$-$C_{30}$ alkyl chains with 0, 1 or 2 ethylenically unsaturated bonds, and
X is absent or selected from the group consisting of —(C=O)—O—; —(C=O)—NH—; —(C=O)—S—; —NH—; —CH=N—; and/or —S—(O=C)—;

(e) the amphiphilic substance is a 1,4- or 1,5-dicarboxylic acid such as aspartic acid, glutamic acid, malic acid, tartaric acid, citric acid, aconitic acid, citraconic acid and/or maleic acid esterified with linear $C_8$-$C_{30}$ alcohols, and/or (f) the amphiphilic substance is a 1,4- or 1,5-diamine of 3-aminoalanine, diaminobutyric acid, ornithine, or lysine amidated with linear $C_8$-$C_{30}$ fatty acids.

The invention therefore relates to the teaching that conjugation of amphoteric groups via a spacer to an amphiphilic substance which can be incorporated in liposomal membranes allows providing structures which, in particular, can be used in the production of liposomes suitable for use in a living organism and capable of binding and/or conveying large amounts of proteins, peptides, carbohydrates, DNA and/or RNA. Surprisingly, the new compounds are suitable in the production of vesicles or liposomes which do not aggregate in blood or serum, are not attacked by complement components, are not cytotoxic, and are stable in blood or serum for several hours, the permeability of the liposomes depending on the pH value and thus on the state of charge of the compounds. That is, the release of active substances by these non-aggregating, stable, non-cytotoxic liposomes depends on the pH value of the medium.

Depending on the amphoteric and amphiphilic substances used, compounds are obtained which alter their charge at a pH value between 4 and 9 and, surprisingly, can be incorporated in liposomal membranes in large amounts.

In the context with this invention, the following abbreviations will be used:
CHEMS Cholesterol hemisuccinate
PC Phosphatidyl choline
PE Phosphatidyl ethanolamine
PS Phosphatidyl serine Amphiphilic Substance Said one or two long-chain alkyls or acyls present in this molecular component comprise between 8 and 30 C atoms. They are preferably linear or slightly branched and may have 0, 1, or 2 ethylenically unsaturated bonds. Particularly preferred are substituents as found in natural lipids, i.e., straight-chain fatty acids or alcohols having 12 to 20 C atoms, with zero, one or two unsaturated bonds. Still more preferred are lauroyl, myristoyl, palmitoyl, stearoyl, oleoyl, and linoleoyl residues or the corresponding fatty alcohols thereof.

Diacylglycerols, dialkylglycerols, phosphoglycerols, acylated or alkylated 3-amino-1,2-propanediols, as well as N,N-dialkylamines are preferably employed as amphiphilic substances, because these compounds, in particular, are available at low cost, involve ordinary chemistry, and allow incorporation in membranes in high amounts without increasing the permeability thereof or even completely destroying their membrane character.

In an advantageous embodiment of the invention, dicarboxylic acids are used as polar head group of the amphiphilic substance, conveniently allowing coupling of the actually charge-bearing substituents via additional functional groups. Representative of the amphiphilic substances derived therefrom are preferably long-chain esters of 1,4- or 1,5-dicarboxylic acids such as aspartic acid, glutamic acid, malic acid, tartaric acid, citric acid, aconitic acid, citraconic acid, maleic acid or similar compounds with fatty alcohols. Particularly preferred are lauryl, myristyl, palmityl, stearyl, oleyl, and linoleyl esters of the above-mentioned dicarboxylic acids. Additional molecular components (spacer, amphoteric substance) are coupled via the remaining amino group, hydroxyl group, carboxylic group, or via the double bond.

Other advantageous amphiphilic substances are obtained from diamines with an additional functional group, e.g. in the form of a diamide of 3-aminoalanine, diaminobutyric acid, ornithine, or lysine with long-chain fatty acids. Particularly preferred amongst these are lauroyl, myristoyl, palmitoyl, stearoyl, oleoyl, and linoleoyl residues.

Ultimately, the compounds according to the invention can also be produced in the form of derivatives of sphingosine or ceramide. They can also be prepared as derivatives of long-chain vinyl ethers or of plasmalogens.

The amphiphilic substances used with advantage as starting materials can be functionalized in their hydrophilic head group in various ways so as to conveniently allow stable, yet biologically degradable coupling or optionally assume the function of a spacer. Particularly suitable for direct coupling is the hydroxyl group that is present, or an amino group. Also suitable are carboxylic groups.

Amphoteric Substance

The overall molecule assumes its pH-dependent charge characteristics by the simultaneous presence of cationic and anionic groups in the "amphoteric substance" molecule portion. More specifically, an amphoteric substance is characterized by the fact that the sum of its charge components will be precisely zero at a particular pH value. This point is referred to as isoelectric point (IP). Above the IP the compound has a negative charge, and below the IP it is to be regarded as a positive cation, the IP of the compounds according to the invention ranging between 4.5 and 8.5.

The overall charge of the molecule at a particular pH value of the medium can be calculated as follows:

$$z = \Sigma n_i \times ((q_i - 1) + (10^{(pK-pH)}/(1 + 10^{(pK-pH)})))$$

$q_i$: absolute charge of the ionic group below the pK thereof (e.g. carboxyl=0, single-nitrogen base=1, di-esterified phosphate group=−1)

$n_i$: number of such groups in the molecule

For example, a compound according to the invention is formed by coupling the amino group of histidine to dipalmitoylglycerol hemisuccinate. At a neutral pH value of 7, the product has a negative charge because the carboxyl function which is present therein is in its fully dissociated form, and the imidazole function only has low charge. At an acid pH value of about 4, the situation is reversed: the carboxyl function now is largely discharged, while the imidazole group is essentially fully protonated, and the overall charge of the molecule therefore is positive.

When using phospholipids as amphiphilic substances, the phosphate constant negative charge present therein has to be compensated by an additional positive charge in order to form a compound according to the invention. One compound intended to illustrate the teaching of the invention is formed by coupling histidine to phosphatidyl serine. In this case, it is irrelevant whether coupling takes place between the carboxyl group of histidine and the amino group of PS or between the amino group of histidine and the carboxylic function of PS. In both cases, molecules are formed wherein a free amino group neutralizes the constant negative charge of the phosphate group. The remaining carboxylic group and the imidazole function react as above, producing the intended characteristics of the structures according to the invention.

In a preferred embodiment of the invention the molecule has an isoelectric point between 4 and 8, preferably between 5 and 7.

In another preferred embodiment of the invention, the amphoteric substance has one or more cations with a $pK_a$ value of between 4 and 8 and, at the same time, one or more anions with a $pK_a$ value of between 3 and 7. In particular, the amphoteric substances can be composed of two charge carriers which both alter their charge in the above-mentioned pH range of between 4 and 9. The simultaneously occurring loss of anionic charge and gain of cationic charge results in a change of charge in the overall molecule.

A particularly preferred embodiment comprises amphoteric substances where the $pK_a$ values of cation and anion are 2 pH units apart at maximum. This is particularly advantageous to the sharpness of the 12. The closer the two $pK_a$ are together, the more narrow the pH range wherein the molecule charge changes from cationic to anionic. An advantageous selection as to type and number of cations and anions can be made by a person skilled in the art with reference to the above-mentioned formula.

It may be convenient to use functional groups or molecule fragments as charge carriers, which are in dissociated form in a pH range between 4 and 9. More specifically, these include phosphoric acid groups, sulfonic acid groups or other strong anions. Also preferred are most of the primary, secondary or tertiary amino groups, including quaternary ammonium, amidinium, pyridinium, and guanidino groups. A particularly advantageous example of the above molecular component is the phosphoric acid group of phospholipids.

According to the invention, these fixed charges of the amphoteric substance must be overcompensated by the variable charges described above. This is only possible when using an excess of variable charge carriers. When using a tertiary amine as cation, for example, at least 2 carboxyl groups are required in order to obtain an amphoteric substance in the meaning of the invention. In case of only one carboxylic group, it is only possible to compensate the positive charge of the amine, and the molecule can never be completely recharged. One advantage when using fully dissociated groups is their strong polarity.

In a particularly preferred fashion, the amphoteric substances can be in the form of complete structural moieties. For example, this is the case with o-, m- or p-aminobenzoic acids, imidazolecarboxylic acid, imidazolediacetic acid, but also nicotinic acid or picolinic acid.

For example, other advantageous compounds are ω-(1-piper-azino)alkylcarboxylic acids, urocanic acid, 4-(2-amino-ethyl)imidazole-maleic acid monoamide, 4-(2-hydroxyethyl)-imidazole-maleic acid monoester, (2-aminoethyl)morpholine-maleic acid monoamide or analogous compounds.

pH-Sensitive Cations with a $pK_a$ Between 4 and 8:

The cation preferably is an imidazole, a piperazine, morpholine, purine, or pyrimidine. Other advantageous cations having this property essentially include nitrogen bases. Particularly in those cases where the nitrogen bases are in the form of a ring system, positional isomers advantageously are existing, wherein the linking spacer is substituted on various positions of the organic cation. Conveniently, the $pK_a$ values of the organic cations can be influenced via said positional isomerism. The relevant fundamental rules are well-known to those skilled in the art. Alternatively, these effects can be estimated from tabular compilations (Handbook of Chemistry and Physics, Vol. 73, pp. 8-37ff.).

More specifically, advantageous organic cations are represented by the following classes of substances:

o-, m-, p-anilines; 2-, 3- or 4-substituted anisidines, toluidines or phenetidines; 2-, 3-, 5-, 6-, 7- or 8-substituted benzimidazoles, 2-, 3-, 4- or 5-substituted imidazoles, 1- or 5-substituted isoquinolines, 2-, 3- or 4-substituted morpholines, 2-, 3- or 4-substituted picolines, 1-, 2- or 3-substituted piperazines, 2-, 5- or 6-modified pterines, 3-, 4-, 5-, 6- or 9-substituted purines, 2- or 3-substituted pyrazines, 3- or 4-substituted pyridazines, 2-, 3- or 4-modified pyridines, 2-, 4-, 5- or 6-substituted pyrimidines, 1-, 2-, 3-, 4-, 5-, 6- or 8-substituted quinolines, 2-, 4- or 5-substituted thiazoles, 2-, 4- or 6-substituted triazines, or derivatives of tyrosine.

Particularly preferred are the above-mentioned piperazines, imidazoles and morpholines, purines or pyrimidines. Highly preferred are molecule fragments such as occurring in biological systems, i.e., for example: 4-imidazoles (histamine, histidine itself), 2-, 6- or 9-purines (adenines, guanines, adenosines, or guanosines), 1-, 2- or 4-pyrimidines (uracils, thymines, cytosines, uridines, thymidines, cytidines), or pyridine-3-carboxylic acids. The above-mentioned structural fragments may also have additional substituents. For example, these can be methyl, ethyl, propyl, or isopropyl residues, more preferably in hydroxylated form, including one or two hydroxyl groups. Also, these can be hydroxyl or keto functions in the ring system.

For example, nitrogen bases with preferred $pK_a$ values are also formed by single or multiple substitution of an amine with lower alkanehydroxyls such as hydroxymethyl or hydroxyethyl groups. Suitable organic bases from this group are e.g. aminopropanediols, triethanolamines, tris(hydroxymethyl)methylamines, bis(hydroxymethyl)methylamines, tris-(hydroxyethyl)methylamines, bis(hydroxyethyl)methylamines, or the appropriately substituted ethylamines.

Nitrogen bases with preferred $pK_a$ values can also be found amongst aminosugars or aminosugar alcohols.

pH-Sensitive Anions of the Amphoteric Substance with a $pK_a$ Between 3 and 7:

In a preferred fashion the anionic charge carriers are carboxylic groups. Obviously, any carboxylic acid can be used as charge carrier. In particular, these include aliphatic straight-chain or branched carboxylic acids with up to 8 C atoms and 0, 1 or 2 ethylenically unsaturated bonds. Exemplary components of compounds are the carboxyl group itself, acetic acid, bromoacetic acid, chloroacetic acid, acetoacetic acid, propionic acid, acrylic acid, butyric acid, crotonic acid, or higher carboxylic acids bound in the aliphatic chain, dicarboxylic acids such as oxalic acid, malonic acid, succinic acid, maleic acid, fumaric acid, malic acid, tartaric acid, glutaric acid, adipic acid, caprylic acid, pimelic acid, suberic acid, cyclohexanedicarboxylic acid or cyclopentanedicarboxylic acid, mono-esterified or amidated or bound in the aliphatic chain, oligocarboxylic acids such as citric acid, isocitric acid or ethylenediaminetetraacetic acid, mono-esterified or amidated or bound in the aliphatic chain.

Other advantageous components of compounds are glycolic acid, lactic acid, hydroxybutyric acid, malic acid, tartaric acid, aspartic acid or glutamic acid, alanine, glycine, serine, threonine, asparagine, glutamine, proline, tyrosine or cysteine, or other amino acids or hydroxy acids, bound in the side chain via a heteroatom.

Carboxylic acids with suitable properties can also be found as substituents of aromatic systems, e.g. as benzoic acid, anisic acid, o-, m- or p-hydroxybenzoic acid, as dihydroxybenzoic acid, gallic acid, cinnamic acid, phenylacetic acid, hippuric acid, phthalic acid, terephthalic acid, 2-, 3- or 4-pyridinecarboxylic acid, furancarboxylic acid. Other anionic groups are dissociable hydroxyls or thiols, such as occurring in ascorbic acid, N-substituted alloxan, N-substituted barbituric acid, in veronal, phenol, or as a thiol group.

Peptides as Amphoteric Substances:

In a preferred embodiment of the invention, the amphoteric substances are peptides including from 2 to 6 amino acids. In another embodiment, particularly the amino acids histidine, arginine, lysine, glutamic acid, or aspartic acid are used in a particularly preferred fashion to form the amphoteric substance and determine the charge characteristics thereof. Other preferred amino acids are glycine, serine, threonine, glutamine, asparagine, but also cysteine, which contribute to increase the polarity and thus enhance the solubility of the amphoteric substance. Particularly preferred compositions of such peptides are shown in the following Table 1 as percentage of total amino acids:

TABLE 1

| Amino acid | His | Arg/Lys | Asp/Glu | Conditions |
|---|---|---|---|---|
| i | Up to 66% | — | Up to 66% | His, Asp/Glu ≠ 0 |
| ii | — | <50% | >Arg/Lys | Arg/Lys, Asp/Glu ≠ 0 |
| iii | ≤33% | ≤33% | >Arg/Lys | all ≠ 0 |

Therein, i) illustrates the case of two pH-sensitive components, ii) the case of one fixed and one pH-sensitive component, and iii) the case of a mixture of i) and ii). The sequence of the individual amino acids is arbitrary, the overall composition mainly determining the charge characteristics. Terminal group of the peptide are blocked in the form of an amide in the case of the C terminus, and with acetyl in the case of the N terminus.

Spacer:

Situated between the amphoteric substance and amphiphilic substance are the molecule fragments: -Y-spacer-X. The spacer is a lower alkyl residue of linear, branched or cyclic structure, which has from 0 to 8 C atoms and includes 0, 1 or 2 ethylenically unsaturated bonds. The spacer may have hydroxyl groups so as to increase the polarity of the molecule. In particular, the spacer can be a sugar, and advantageously a polyethylene glycol which may comprise up to 20 monomer units.

X and Y:

In a preferred fashion the linking group X comprises the structures —(C=O)—O—; —(C=O)—NH—; —NH—(C=O)—O—; —O—; —NH—; —CH=N— or —S—S—. Advantageously, the linking group Y may correspond in its structure to the group X, and may additionally comprise the structures —O—(O=C)—; —S—(O=C)—; —NH—(O=C)—; —O—(O=C)—NH—; or —N=CH—. X and/or Y can also be deletions, i.e., their presence is not required. For example, the Y group can be omitted in those cases where the amphoteric substance can be coupled directly to the amphiphilic substance, e.g. in the esterification of imidazole-4,5-dicarboxylic acid with dipalmitoylglycerol.

Synthetic Methods:

Methods of performing chemical coupling of the individual molecule components are well-known to those skilled in the art and may vary depending on the starting material that is used and on the coupling component. Typical reactions are esterification, amidation, addition of amines to double bonds, etherification, or reductive amination.

Particularly preferred molecules can be prepared by i) esterification of diacylglycerols,
ii) esterification or amidation of diacylglycerol hemisuccinate,
iii) addition of amines to the double bond of a diacylglycerol hemimaleate,
iv) amidation of phosphatidyl ethanolamine or phosphatidyl serine, v) amidation or alkylation of 3-amino-1,2-propanediol diesters,
vi) oxidation of phosphatidyl glycerols and subsequent reductive Amination, and
vii) reductive amination of glyceraldehyde and subsequent acylation.

Particularly preferred compounds include the following embodiments (long-chain hydrocarbon chains of the amphiphilic substances are represented in abbreviated spelling, corresponding to lauroyl, myristoyl, palmitoyl, stearoyl, oleoyl and linoleoyl residues):
Phospholipids

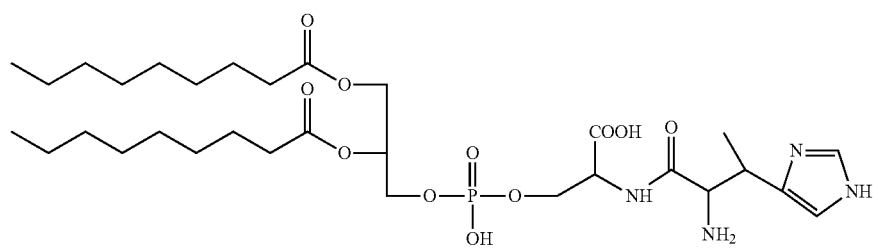 [SMILES: CCCCCCCCC(=O)OCC(COP(=O)(O)OCC(NC(=O)C(N)C(C)c1c[nH]cn1)C(=O)O)OC(=O)CCCCCCCC]

7 Histidinylphosphatidyl serine by coupling of histidine to the amino group of phosphatidyl serine

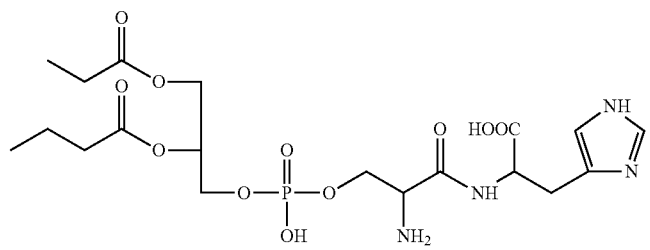 [SMILES: CCCC(=O)OC(COC(=O)CC)COP(=O)(O)OCC(N)C(=O)NC(Cc1c[nH]cn1)C(=O)O]

26 Phosphatidyl serylhistidine by coupling of histidine to the carboxyl group of phosphatidyl serine

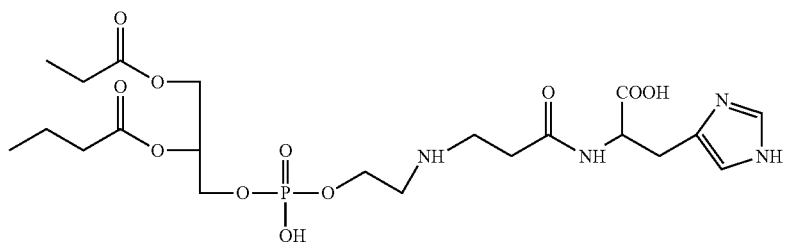 [SMILES: CCCC(=O)OC(COC(=O)CC)COP(=O)(O)OCCNCCC(=O)NC(Cc1c[nH]cn1)C(=O)O]

25 Derivative of phosphatidyl glycerol. Coupling of carnosine is effected according to reaction vi).

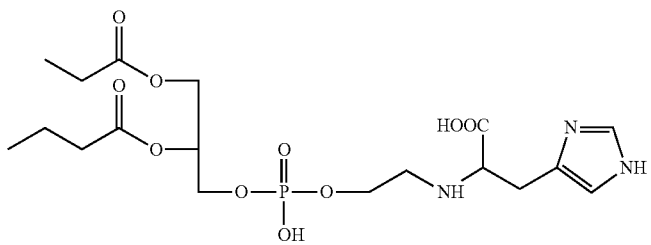 [SMILES: CCCC(=O)OC(COC(=O)CC)COP(=O)(O)OCCNC(Cc1c[nH]cn1)C(=O)O]

29 Derivative of phosphatidyl glycerol. Coupling is effected according to reaction vi) with histidine.

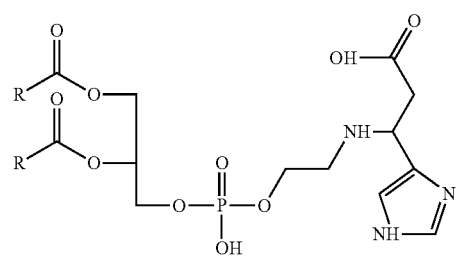

28 N-Phosphatidyl ethyl-3-amino-5-imidazoylcarboxylic acid:
a) addition of phosphatidyl ethanolamine to urocanic acid according to iii) or b) according to vi) with β-histidine and phosphatidyl glycerol -continued

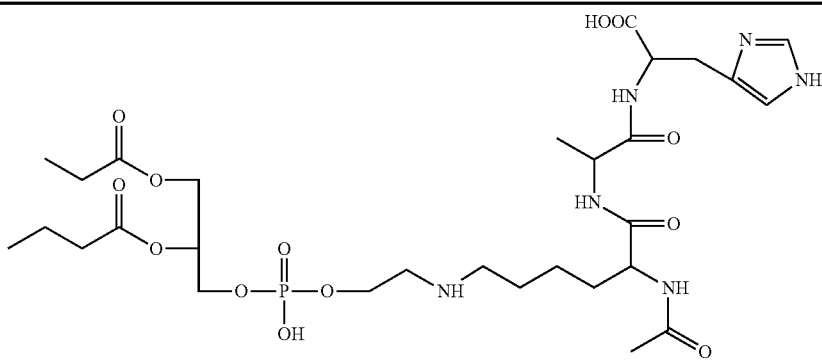

31 Acetyl-Lys-Ala-His coupled via the side chain amino group of Lys to DPPG according to vi)

1-Amino-2,3-Propanediols

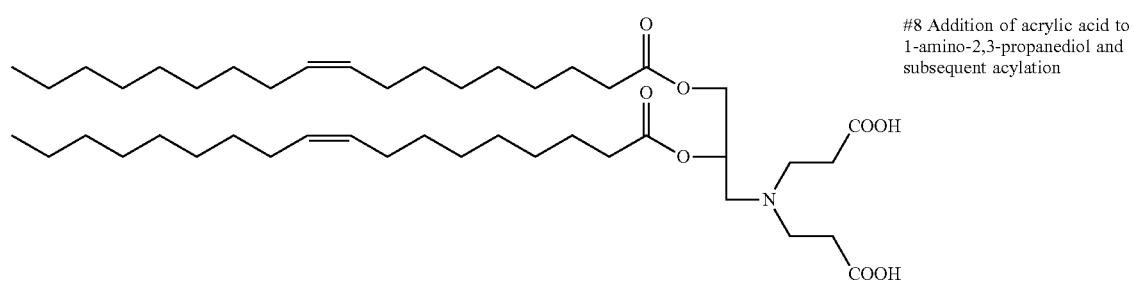

8 Addition of acrylic acid to 1-amino-2,3-propanediol and subsequent acylation

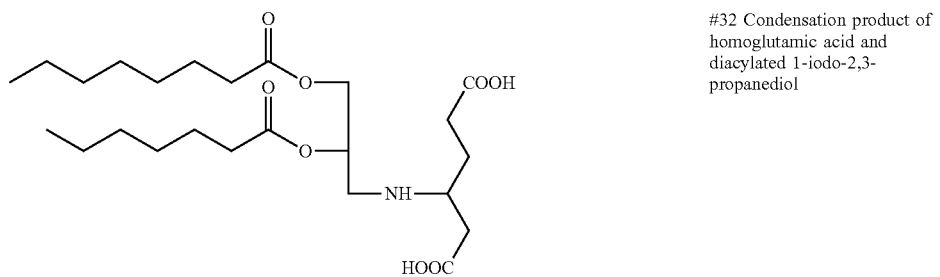

32 Condensation product of homoglutamic acid and diacylated 1-iodo-2,3-propanediol

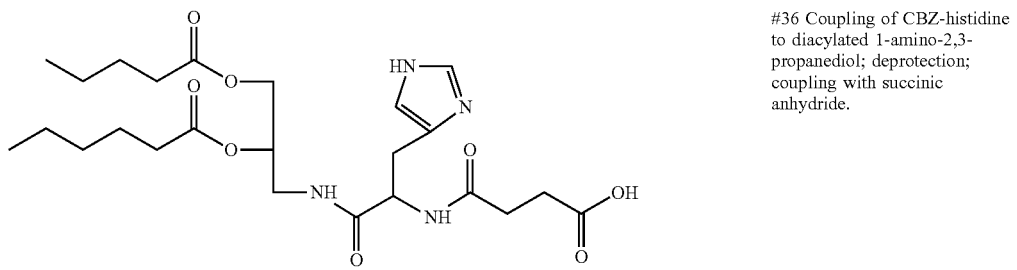

36 Coupling of CBZ-histidine to diacylated 1-amino-2,3-propanediol; deprotection; coupling with succinic anhydride.

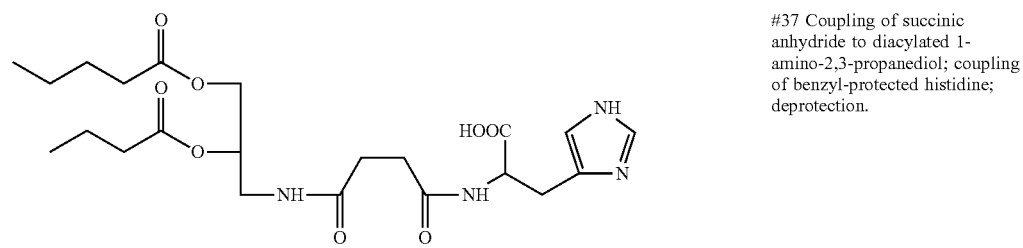

37 Coupling of succinic anhydride to diacylated 1-amino-2,3-propanediol; coupling of benzyl-protected histidine; deprotection.

-continued

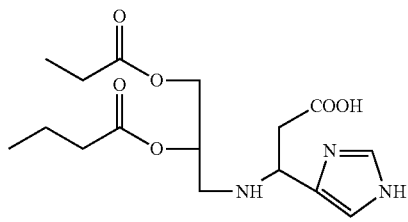 [SMILES: CCCC(=O)OC(CNC(CC(=O)O)c1c[nH]cn1)COC(=O)CC]

38 Conjugation of β-histidine to diacylated 1-iodo-2,3-propanediol

Diacylglycerols

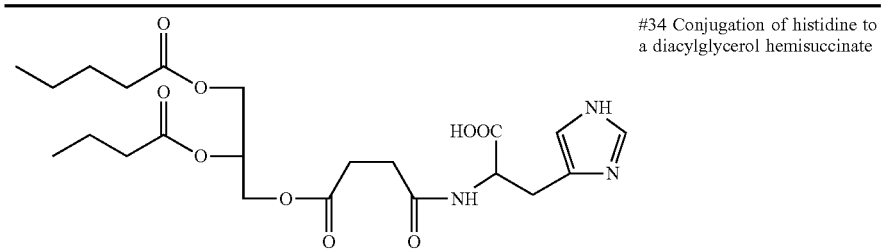

34 Conjugation of histidine to a diacylglycerol hemisuccinate

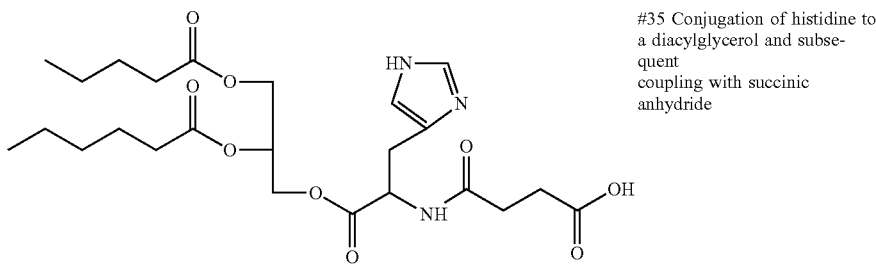

35 Conjugation of histidine to a diacylglycerol and subsequent coupling with succinic anhydride Dicarboxylic Acids and Diamines The long-chain amphiphilic substances are represented in abbreviated spelling, corresponding to lauryl, myristyl, palmityl, stearyl, oleyl, and linoleyl residues.

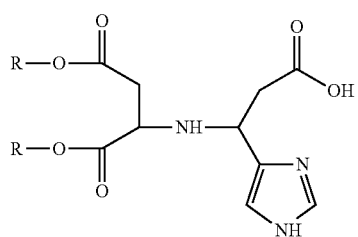

50 N-(Aspartic acid dihydroxyalkyl)-3-amino-5-imidazolecarboxylic acid, can be prepared by addition of aspartic acid diester to urocanic acid.

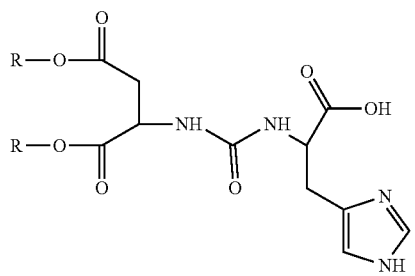

51 N-(Aspartyldihydroxyalkyl)-N'-histidinylurea

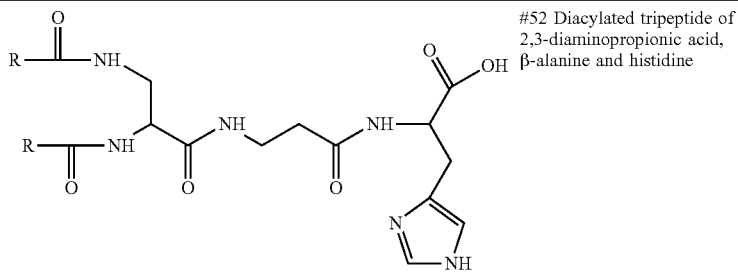

52 Diacylated tripeptide of 2,3-diaminopropionic acid, β-alanine and histidine

Particularly preferred amphoteric components include e.g. the following compounds wherein $R_1$ and $R_2$ represent the amphiphilic substance and ( )n additional molecule portions according to the spacer defined above.

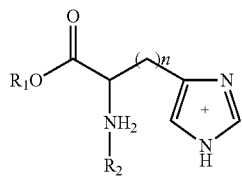

Histidine derivatives Coupling of the amphiphilic substance preferably proceeds via the amino group as $R_2$. In this event, $R_1$ is an anion and can be e.g. H or a hydroxycarboxylic acid or one or more amino acids. Where coupling proceeds via $R_1$, $R_2$ is an anionic residue, e.g. a carboxylic acid or dicarboxylic acid.

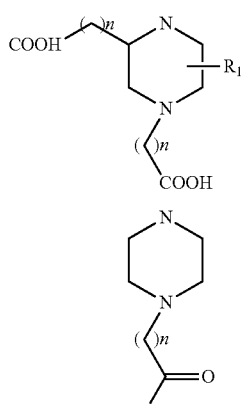

Piperazine derivatives Coupling of the amphiphilic substance may proceed via one of the ring atoms. In those cases where the side chains are hydroxycarboxylic acids or amino acids, coupling may proceed with advantage via these heteroatoms. The preferred derivative on the left shows coupling of piperazine to the Nα of phosphatidyl serine.

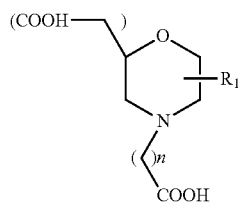

Morpholine derivatives Coupling of the amphiphilic substance may proceed via one of the ring atoms. In those cases where the side chains are hydroxycarboxylic acids or amino acids, coupling may proceed with advantage via these heteroatoms.

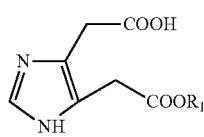

Derivatives of imidazole-4,5-diacetic acid. Coupling of the amphiphilic substance preferably proceeds as an ester via any of the two acetic acid functions. The amphiphilic substance may also be bound via the 3-amino function.

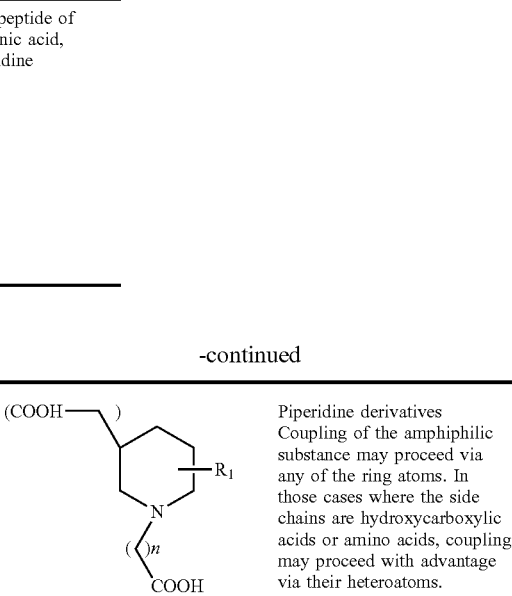

Piperidine derivatives Coupling of the amphiphilic substance may proceed via any of the ring atoms. In those cases where the side chains are hydroxycarboxylic acids or amino acids, coupling may proceed with advantage via their heteroatoms.

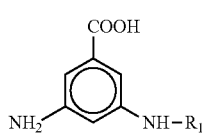

Diaminobenzoic acid derivatives Coupling of the amphiphilic substance preferably proceeds via any of the two amino groups. The second amino group can be alkylated, for example, so as to obtain a higher $pK_a$ value. Coupling as an amide of phosphatidyl serine is another preferred embodiment of the invention.

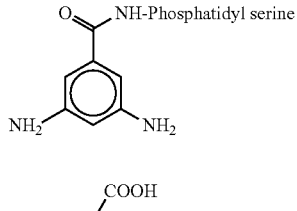

Nitrilotriacetic acid derivatives Amphoteric groups are also formed by esterification of nitrilotriacetic acid. In addition, the charge properties of such compounds can be modified by complexing of metal ions.

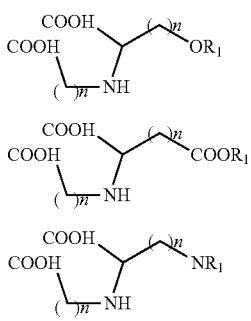

N-Alkylcarboxyamino acid derivatives Amphoteric compounds are also formed by coupling of sterols to the terminal groups of N-acylamino acids. Advantageously, the structure can be derived from serine, aspartic acid or glutamic acid, or from lysine or ornithine. Coupling of the aminodicarboxylic acids not only can be at the terminus, but also at the other acid groups. In addition, the charge properties of such compounds can be modified by complexing of metal ions.

-continued

| | |
|---|---|
| 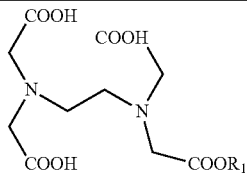 | EDTA derivatives Amphoteric groups are also formed by esterification of ethylene-diaminetetraacetic acid. In addition, the charge properties of such compounds can be modified by complexing of metal ions. |

The invention also relates to liposomes comprising the compounds according to the invention. The compounds of the invention can be incorporated in high amounts in liposomal membranes to form amphoteric liposomes which are characterized in that their state of charge undergoes a reversible change when changing the pH of the surrounding medium. The liposomes are cationic below their isoelectric point, and anionic above said point.

Liposomes comprising the components of the invention can be coated with polymers under suitable conditions, where single or multiple deposition of such substances on the surface is possible. In multiple deposition, optionally in the presence of crosslinkers, liposomal nanocapsules are formed. Methods of producing said liposomes are known to those skilled in the art e.g. from WO 00/28972 or WO 01/64330 which hereby are incorporated by reference and thus deemed part of the disclosure. One particularly advantageous fact when using the substances according to the invention is that the electrostatic interaction with the polymer can be interrupted if said polymer is a polyelectrolyte. As is well-known, the interaction of a polyelectrolyte with charge carriers of the liposomal membrane may give rise to demixing of membrane components and formation of lipid clusters. In many cases, such demixing is accompanied by a permeabilization of the liposomes. The substances of the invention allow elimination of this interaction subsequent to the coating process. When increasing the pH value to or above the IP at this point in time, the liposomes will be entrapped in the nanocapsules merely in a steric fashion, and interaction between the membrane and the polyelectrolytes does no longer exist. Advantageously, cluster formation of lipids and associated permeabilization of the membrane can be circumvented in this way.

Surprisingly, it has been found that liposomes including the substances of the invention in the membrane thereof readily undergo fusion with other membranes, particularly cell membranes, below the isoelectric point of the substance. In general, this step requires the presence of a major amount of PE in the membrane. As a result of its tendency of forming hexagonal phases, said PE assumes the function of a helper lipid. However, the inferior stability of such membranes is disadvantageous, and gradual release of entrapped active substances is frequently observed.

Advantageously, liposomes produced using the substances according to the invention undergo effective fusion even in the absence of helper lipids. Thus, when using the substances of the invention, it is possible to produce liposomes which are capable of stably encapsulating an active substance, but undergo fusion with cell membranes under the conditions of low pH values to release the active substance there.

In a preferred embodiment of the invention, the proportion of amphoteric lipids comprises 30 mole-%, 40 mole-% or 50 mole-% of total lipids at maximum. Compositions comprising at least 2 mole-% of amphoteric lipids, but 50 mole-% at maximum, are particularly advantageous. Compositions comprising at least 5 mole-% of amphoteric lipids, preferably 10 mole-%, and 50 mole-% at maximum, and preferably 40 mole-% are particularly preferred. The production of liposomes comprising the substances of the invention proceeds according to techniques well-known to those skilled in the art.

In another preferred embodiment of the invention, the liposomes comprise phosphatidyl choline, phosphatidyl ethanolamine, diacylglycerols, ceramides, sphingolipids, tetraether lipids and/or PEG lipids. The inventive compounds do not always form liposomes by themselves, and it may therefore be advantageous to add the above-mentioned lipids.

In another preferred embodiment of the invention, the liposomes have an average size between 50 and 1000 nm, preferably between 50 and 500 nm, more preferably between and 300 nm and especially preferably between 60 and 130 nm.

Conveniently, particularly water-soluble active substances are enclosed in the liposomes, which substances can be used e.g. in cancer therapy and in the therapy of severe infections. To this end, liposome dispersions can be injected, infused or implanted. Thereafter, they are distributed in the blood or lymph or release their active substance in a controlled fashion as a depot. The latter can be achieved by highly concentrated dispersions in the form of gels. The liposomes can also be used for topical application on the skin. In particular, they may contribute to improved penetration of various active substances into the skin or even passage through the skin and into the body. Furthermore, the liposomes can also be used in gene transfer. Due to its size and charge, genetic material is usually incapable of entering cells without an aid. For this purpose, suitable carriers such as liposomes or lipid complexes are required which, together with the DNA, are to be taken up by the respective cells in an efficient and well-directed fashion. More advantageously, the active substance is a protein, a peptide, a DNA, RNA, an antisense nucleotide, and/or a decoy nucleotide. In their principal structure, liposomes are highly similar to cell membranes. Therefore, they can be used as membrane models to quantify the permeation rate of active substances through membranes or the membrane binding of active substances.

In another preferred embodiment of the invention, at least 50 µg, more advantageously 100 µg, preferably 150 µg of active substance per mg lipid is entrapped in the liposomes. If necessary, non-incorporated cargo molecules adhering on the outside can be removed by simply increasing the pH value. This step is necessary in all those cases where non-incorporated cargo molecules would give rise to aggregation of the liposomes. One advantageous fact when using the components of the invention is that the entrapped active substances must be maintained under conditions allowing interaction with the lipid layer only during the period of actual enclosure. Once the lipid layer remains closed in itself, it is possible to change to other conditions. Thereby, possible inactivation of active substances, particularly of proteins, can be minimized.

The invention also relates to methods of loading liposomes with active substances, using a binding pH value for encapsulation and a second pH value to remove unbound active substances.

Furthermore, the invention relates to a method of loading liposomes with active substances, wherein the liposomes are made permeable at a specific pH value and subsequently sealed. In particular, changes in permeability preferably can be used in a well-directed fashion in loading liposomes. To this end, an active substance to be enclosed can be added to a medium under conditions of high permeability, followed by adjusting conditions of low permeability. In this way, the active substance will remain inside the liposomes. Thereafter, non-entrapped active substance can be removed, if necessary. Such changes in permeability can be induced on liposomes or on liposomal nanocapsules.

The invention also relates to the use of the liposomes in diagnostics and in release systems. Obviously, the liposomes can also be used in a detection system. In particular, the liposomes can be loaded with metal ions whose fluorescence is enhanced by chelate formation, i.e., terbium or europium ions, for example. Liposomes for such uses may of course include components determining the specificity, i.e., antibodies, lectins, selectins, receptors, or hormones, or RNA aptamers. In a particularly preferred embodiment of the use according to the invention, the presence of these metal ions is restricted to the volume of the liposomes so as to avoid non-specific signals from slowly released metal ions adhering on the outside. It is also convenient to use the liposomes in the production of nanocapsules. The liposomes can be used with advantage in the production of release systems in diagnostics.

The use for transport and/or release of active substances is also convenient. Advantageously, the liposomes can be used as depot formulation and/or as circulative depot. The use of the liposomes as a vector to transfect cells in vivo, in vitro and/or ex vivo is also advantageous. For example, the liposomes can be used in intravenous and/or peritoneal application.

The compounds and liposomes according to the invention involve several advantages. Surprisingly, it has been determined that the permeability of the inventive liposomes depends on the pH value and thus, on the state of charge of said compounds.

Liposomes produced using the structures according to the invention are therefore particularly suited to construct release systems wherein release of active substances is to proceed in dependence on the pH value of the medium.

Surprisingly, it has also been found that amounts of proteins or DNA above average, at least 50 µg, preferably 100 µg, more preferably 150 µg per mg of lipid, can be enclosed in liposomes including the compounds of the invention in the membranes thereof. The efficiency of such incorporation depends on the pH value of the solution employed. Therefore, a process for efficient encapsulation of proteins or DNA in liposomes can be performed by initially adjusting a pH value that would result in good binding of the cargo molecules to the lipid layer. With DNA as polyanion, low pH values of about 4 to 5 are used. With proteins, a useful pH value will depend on the isoelectric point of the protein, which should be below the isoelectric point of the substance according to the invention. Encapsulation is particularly effective when the pH value of the medium is selected so as to range between the isoelectric point of the protein and the isoelectric point of the compound according to the invention. The protein then will have a negative charge and the lipid layer a positive charge.

Surprisingly, it has also been found that liposomes including e.g. histidinyl-PS or histidinyldiacylglycerol hemisuccinate in the membranes thereof are capable of chelating metal ions. This property results in an increase of the positive charge of the liposome. This effect is observed to be particularly strong at neutral pH values, because the inherent charge of the compound is low in this case. Owing to their chelating properties, such liposomes can be used in biochemical diagnostics and in pharmaceutical therapy.

One essential precondition for the use of liposomes for experimental or therapeutic purposes is their compatibility with cells and tissues. A number of well-known compounds used to incorporate DNA or proteins in cells (for example, the cationic lipid DOTAP) are cytotoxic. Surprisingly, it has been found that some of the compounds of the invention exhibit reduced cytotoxicity. In particular, this applies to that group of compounds wherein the amphoteric substance is an amino acid or a peptide. These compounds therefore satisfy one of the preconditions of a transfection system.

Another precondition for the construction of vectors to be used in gene or protein transport into cells is their compatibility with serum or blood. Due to their strong cationic charge, vectors known at present form uncontrollable large aggregates, resulting in formation of thrombi in the organism. Their use in vivo is therefore practically impossible and is restricted to in vitro or ex vivo applications. Surprisingly, it has been found that liposomes constructed using the components of the invention do not form any aggregates in serum or blood. In particular, these are liposomes having an isoelectric point below 7.5.

Another precondition for the construction of vectors to be used in protein or gene transfer is their stability under physiological conditions. Upon application into the blood circulation, liposomes are attacked by components of the complement system and undergo rapid lysis. This reaction proceeds within minutes. As a result, pores are formed in the membrane, which allow even large molecules such as proteins to diffuse out, therethrough. At present, stabilization of liposomes with respect to this mechanism is only possible by incorporating cholesterol in the lipid layer. While such liposomes are highly stable, they are no longer able to interact with cells or readily release their active substance. Surprisingly, it has been found that liposomes constructed using the components of the invention can be stable in serum or blood for several hours. Even under such conditions, the release of active substance is low. A liposomal vector for the transport of active substances must satisfy at least three preconditions: it must have low toxicity, entrap the active substance firmly and stably, and be compatible with serum or blood.

Advantageously, all of these three preconditions are satisfied by liposomes produced using selected substances according to the invention. The liposomes are therefore well suited for therapeutic uses. Other properties supporting such uses are good loadability with active substances and well-directed removal of these substances by changing the pH value or by permeabilization of the membrane. Liposomes produced using the substances of the invention show low non-specific binding to cell surfaces. It is this low non-specific binding which is an essential precondition for achieving specific binding to target cells. Target control of the vehicles is obtained when providing the above-described liposomes with additional ligands. As a result, the active substance can be accumulated specifically in such cells or tissues which exhibit a pathological condition.

One important use of the substances according to the invention is therefore in the construction of vectors for transfer of active substances in living organisms. The vectors are particularly suited for the transport of therapeutic macromolecules such as proteins or DNA which themselves are incapable of penetrating the cell membrane or undergo rapid degradation in the bloodstream.

Surprisingly, it has been found that amphoteric amphiphilic substances with only one hydrocarbon chain, such as disclosed in U.S. Pat. No. 6,255,344, are also suitable in the production of amphoteric liposomes according to the invention, provided the hydrocarbon chain has more than 12 CH$_2$ groups. Advantageously, the above liposomes can be loaded with active substance, especially DNA or oligonucleotides, according to the above-mentioned process, and their use in the transfection of cells and in gene therapy is hereby incorporated in the disclosure of the present invention.

Surprisingly, it has also been found that double-chain amphiphilic substances formed by amidation of long-chain fatty acids with long-chain α-aminocarboxylic acids and provided with an amphoteric group such as histidine are also suitable in the production of amphoteric liposomes. Advantageously, such liposomes can be loaded with active substance, especially DNA or oligonucleotides, according to the above-mentioned process, and their use in the transfection of cells and in gene therapy is hereby incorporated in the disclosure of the present invention.

Without intending to be limiting, the invention will be explained in more detail with reference to the following examples.

Example 1

Synthesis of L-Histidinyl-Dipalmitoylglycerol Succinate (DG-Succ-Hist, #34)

To synthesize DG-Succ-Hist, 3 mmol (2 g) of diacylglycerol succinate (Avanti) is reacted with 3.3 mmol (0.81 g) of benzyl-protected histidine, 3.45 mmol (0.71 g) DCC and 3.45 mmol (0.42 g) DMAP in 50 ml of dichloromethane as solvent. The reaction batch is allowed to stir at room temperature overnight. Subsequent to amide coupling, the carbonyl group of the histidine is deprotected by means of catalytic hydrogenolysis on 10% palladium/carbon and stirring under hydrogen atmosphere overnight. The reaction batch is concentrated in vacuum, followed by purification using column chromatography on silica gel 60. Chloroform/methanol/ammonia (25% solution) 60:40:2 is used as eluent.

Example 2

Synthesis of Compound #35 (DG-Hist-Succ)

The synthesis of DG-Hist-Succ is effected in three steps. Initially, 3.7 mmol (2 g) of dipalmitoylglycerol is esterified with 4.1 mmol amino-protected CBZ-histidine. Ester formation is effected adding 4.3 mmol (0.67 g) of EDC and 4.3 mmol (0.53 g) of DMAP in 60 ml of dichloromethane. The batch is stirred for 4 hours. Deprotection of the histidine amino function furnishes the intermediate DG-Hist. The amino group is deprotected by means of catalytic hydrogenolysis on 10% palladium/carbon and stirring under hydrogen atmosphere overnight. In a second step succinic anhydride is opened with benzyl alcohol to form benzyl succinate. 10 mmol (1 g) of succinic anhydride and 9.5 mmol (1 g) of benzyl alcohol are dissolved in 50 ml of toluene. Following addition of 1 mmol (190 mg) of p-toluenesulfonic acid monohydrate, this is heated at reflux for two hours. In the final step 2 mmol (0.42 g) of benzyl-protected succinate is coupled to 1.6 mmol (1.13 g) DG-Hist via an amide bond. The reaction is effected adding 2.5 mmol (0.39 g) of EDC and 2.5 mmol (0.3 g) of DMAP in 50 ml of dichloromethane, with stirring at room temperature for 4 hours. Finally; the succinate is deprotected by cleavage of the benzyl residue using catalytic hydrogenolysis on 10% palladium/carbon and stirring under hydrogen atmosphere overnight. The reaction batch is concentrated in vacuum, followed by purification using column chromatography on silica gel 60. Chloroform/methanol/ammonia (25% solution) 60:40:2 is used as eluent.

Example 3

Synthesis of compound #8, N,N-bis(propanoic acid-3-yl)-N-(2,3-dioleoyloxypropyl)amine The synthesis of the desired compound proceeds via three steps.

In the 1$^{st}$ step the amino group of 3-amino-1,2-propanediol is protected with tert-butyl acrylate. 111 mmol (10 g) of 3-amino-1,2-propanediol is placed in 100 ml of acetonitrile. 222 mmol (28.5 g) of tert-butyl acrylate is added under protective gas, and the batch is heated at reflux for two days. The reaction mixture is concentrated in a rotary evaporator and purified using column chromatography on silica gel. Ethyl acetate/methanol 9:1 is used as eluent.

In the next step 17.7 mmol (6.15 g) of intermediate from step 1 and 35.4 mmol (10 g) of oleic acid are placed in 100 ml of dichloromethane. The reaction is carried out under protective gas and cooling in an ice bath. Following addition of 35.4 mmol (7.3 g) of dicyclohexylcarbodiimide, the ice bath is removed and the batch is stirred at room temperature for one day. The precipitated urea is filtrated off, and the solution is concentrated in a rotary evaporator. The product is put to further use in raw condition. Thereafter, the protective group is removed. To this end, 11.5 mmol of intermediate from step 2 is placed in 25 ml of dichloromethane. 25 ml of trifluoroacetic acid is added slowly under cooling with ice-water. This is stirred at 40° C. for one day. Following removal of the solvent, the residue is purified using column chromatography on silica gel. Ethyl acetate/petroleum ether 1:1 is used as solvent. The resulting oil is taken up in approximately 50 ml of acetone and adjusted to slightly alkaline using 1 N sodium hydrogen carbonate solution. This is centrifuged, and the supernatant is discarded. The residue is treated with a small amount of acetone in an ultrasonic bath, centrifuged, and the supernatant is discarded. The residue is taken up in 30 ml of chloroform, and 30 ml of water is placed as a layer thereon. This is adjusted to pH 5 with 1 N HCl with vigorous stirring. The organic phase is removed, dried over sodium sulfate and concentrated in a rotary evaporator.

Example 4

Preparation of Amphoteric Liposomes 2 mg of the corresponding lipid and 10 mg of DMPC are dissolved in 4 ml of chloroform/methanol (1:1 v/v) and dried completely in a rotary evaporator. The lipid film is hydrated with 4.3 ml of buffer (10 mM Kac, 10 mM HEPES, 150 mM NaCl, pH 7.5) at a lipid concentration of 5 mM using ultrasonic treatment for 5 minutes. Finally, the suspension is frozen and, following thawing, subjected to multiple extrusions (Avestine LiposoFast, polycarbonate filter, pore width 200 nm). The profile of the zeta potential in mV at varying pH values is illustrated in FIG. 1. The zero point indicates the pH value at which the liposome is discharged. This pH corresponds to the isoelectric point of the lipid and is 4.5 for #8, 5.2 for #34, 5.7 for #25.

Unilamellar liposomes (DPPC/DPPG/cholesterol 40:20:40 mole-%) are suspended at a concentration of 20 mM lipid in a borate buffer (20 mM sodium borate, 120 mM sodium chloride, pH 8.4). 2 ml of this solution is added with 400 µl of a 0.6 M sodium periodate solution, and the mixture is incubated for 30 min in the dark. 1 ml of this suspension is chromatographed on Sephadex G25 in the borate buffer used above. The eluate of the liposome suspension is filled up to make 4 ml.

The liposomes thus oxidized are added with carnosine at a final concentration of 20 mM and incubated for 2 hours. Finally, this is reduced with 20 mM sodium borohydride at 4° C. overnight. Excess carnosine can be removed by chromatography on Sephadex G25 as above.

Example 6

Measurement of the Serum Aggregation of Liposomes

140 μl of human serum is added with 10 μl of a 25 mM liposome suspension using a pipette and mixed thoroughly. 65 μl of this mixture is removed and diluted with 1.5 ml of buffer (HEPES 10 mM, NaCl 150 mM, pH 7.5). The remainder is incubated for 2 h at 37° C., followed by removal of another 65 μl and dilution with 1.5 ml of buffer. The particle size is determined in both samples, using a Malvern Zetasizer 3000. In parallel, control samples likewise incubated for 2 hours at 37° C. are recorded in blank buffer. Non-varied particle size indicates good serum compatibility.

Example 7

Preparation of Amphoteric Liposomes Loaded with DNA Plasmids 1.43 mM of the amphoteric lipid is dissolved in chloroform together with the other lipids, depending on the lipid composition of the lipid film. Following removal of the solvent, the lipid film is dried under vacuum overnight.

The lipid film is hydrated directly with 1 ml DNA-containing (100 μg DNA/ml) NaAc buffer (10 mM NaAc, 150 mM NaCl, pH 4; slight ultrasonication, followed by rotation above the phase transition temperature for 30 min). This is followed by a freeze/thaw step.

The mixture is extruded 15 times through 400 nm membranes at a temperature 10° C. above the phase transition temperature.

Non-entrapped DNA can be removed by flotation in a sucrose gradient (at pH 7.5; 0.8 M sucrose, 0.5 M sucrose, buffer). The DNA content is determined using the intercalation dye propidium iodide, an increase in fluorescence intensity occurring in case of intercalation into the DNA. To this end, 20 μl of propidium iodide and 6 μl of Triton X-100 (10% in water) are filled up with sample to make 300 μl and measured using a fluorescent plate reader.

The invention claimed is:
1. An amphoteric lipid having the structure

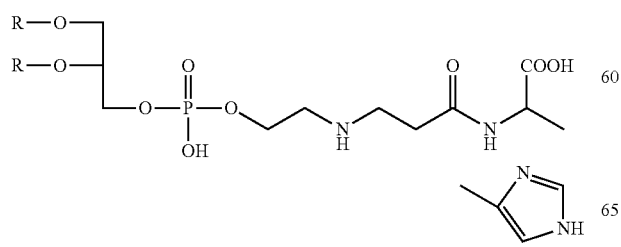

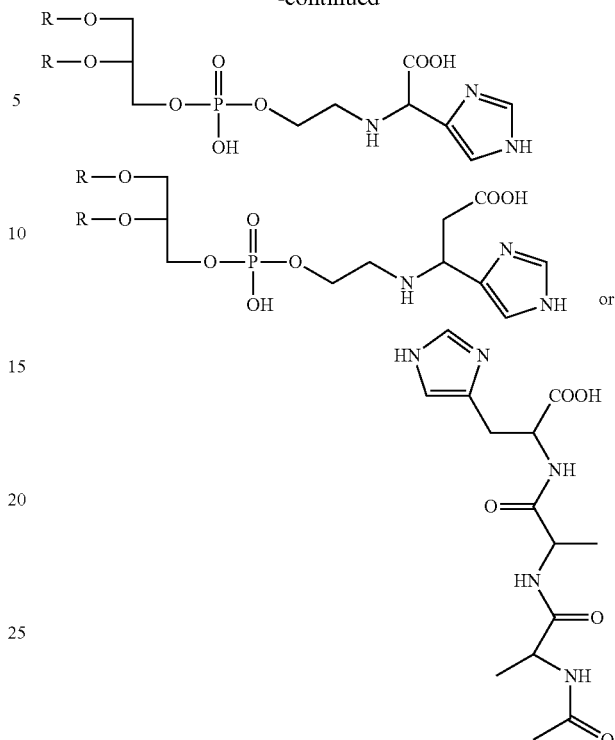

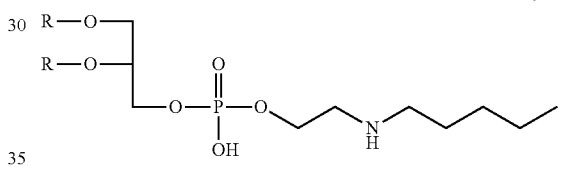

wherein each R is independently selected from lauroyl, myristoyl, palmitoyl, stearoyl, oleoyl and linoleoyl residues; and liposomes thereof.

2. An amphoteric lipid having the structure

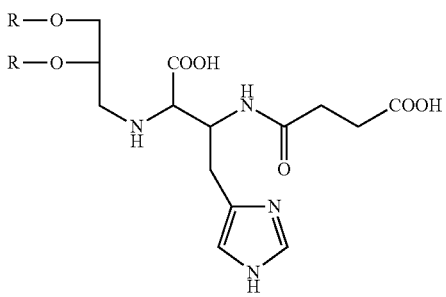

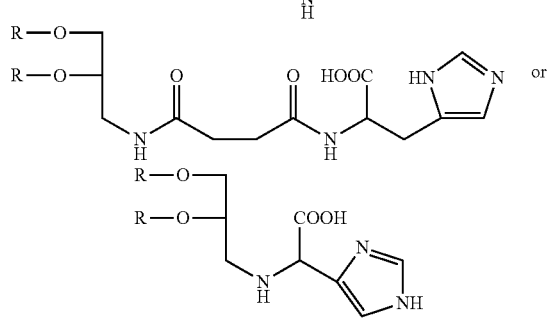

wherein each R is independently selected from lauroyl, myristoyl, palmitoyl, stearoyl, oleoyl and linoleoyl residues, and liposomes thereof.

3. An amphoteric lipid having the structure

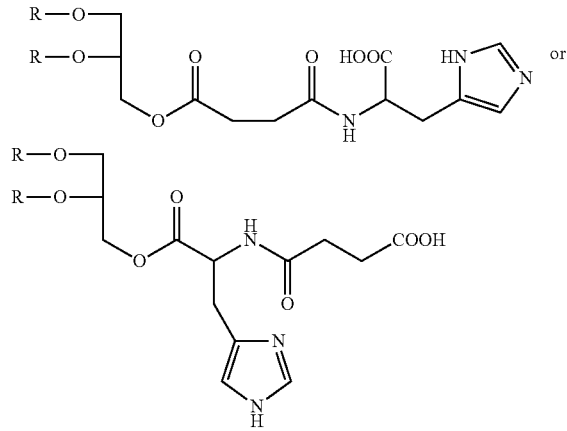

wherein each R is independently selected from lauroyl, myristoyl, palmitoyl, stearoyl, oleoyl and linoleoyl residues, and liposomes thereof.

4. An amphoteric lipid having the structure

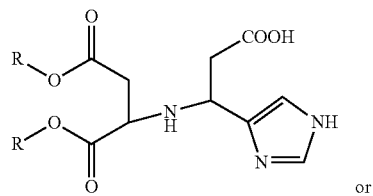

or

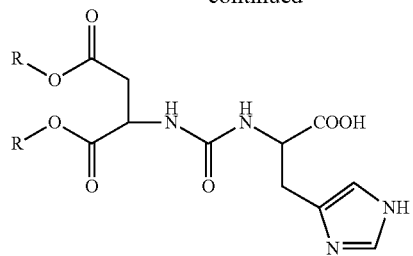

wherein each R is independently selected from lauryl, myristyl, palmityl, stearyl, oleyl and linoleyl residues; and liposomes thereof.

5. An amphoteric lipid having the structure

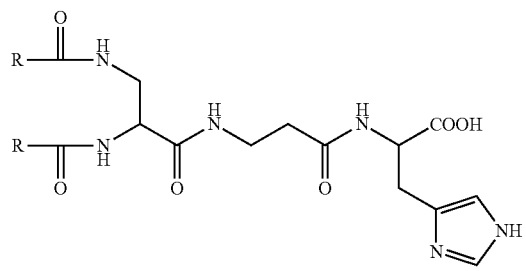

wherein each R is independently selected from lauryl, myristyl, palmityl, stearyl, oleyl and linoleyl residues; and liposomes thereof.

* * * * *